United States Patent [19]
Jöbsis et al.

[11] 4,321,930
[45] * Mar. 30, 1982

[54] APPARATUS FOR MONITORING METABOLISM IN BODY ORGANS

[75] Inventors: Frans F. Jöbsis; Johannes H. Keizer; Ronald F. Overaker, all of Durham, N.C.

[73] Assignee: Duke University, Inc., Durham, N.C.

[*] Notice: The portion of the term of this patent subsequent to Sep. 23, 1997, has been disclaimed.

[21] Appl. No.: 188,578

[22] Filed: Sep. 18, 1980

Related U.S. Application Data

[63] Continuation-in-part of Ser. No. 810,777, Jun. 28, 1977, Pat. No. 4,281,645, and Ser. No. 17,727, Mar. 5, 1979, Pat. No. 4,223,680.

[51] Int. Cl.³ .............................................. A61B 5/00
[52] U.S. Cl. .................................................... 128/633
[58] Field of Search ............... 128/633, 634, 664, 665, 128/687, 688, 689

[56] References Cited

U.S. PATENT DOCUMENTS

| | | | |
|---|---|---|---|
| 3,154,067 | 10/1964 | Stenstrom et al. | 128/687 |
| 3,167,658 | 1/1965 | Richter | 128/687 |
| 3,638,640 | 2/1972 | Shaw | 128/633 |
| 4,086,918 | 5/1978 | Kofsky et al. | 128/633 |

*Primary Examiner*—William E. Kamm
*Attorney, Agent, or Firm*—B. B. Olive

[57] ABSTRACT

A mounting structure secures to a selected portion of the human body, e.g., the head, a limb, or the torso, and incorporates light source and light detecting means adapted for association with spectrophotometric circuitry for in situ, in vivo monitoring of local metabolism in the area of the body where the structure is secured.

11 Claims, 23 Drawing Figures

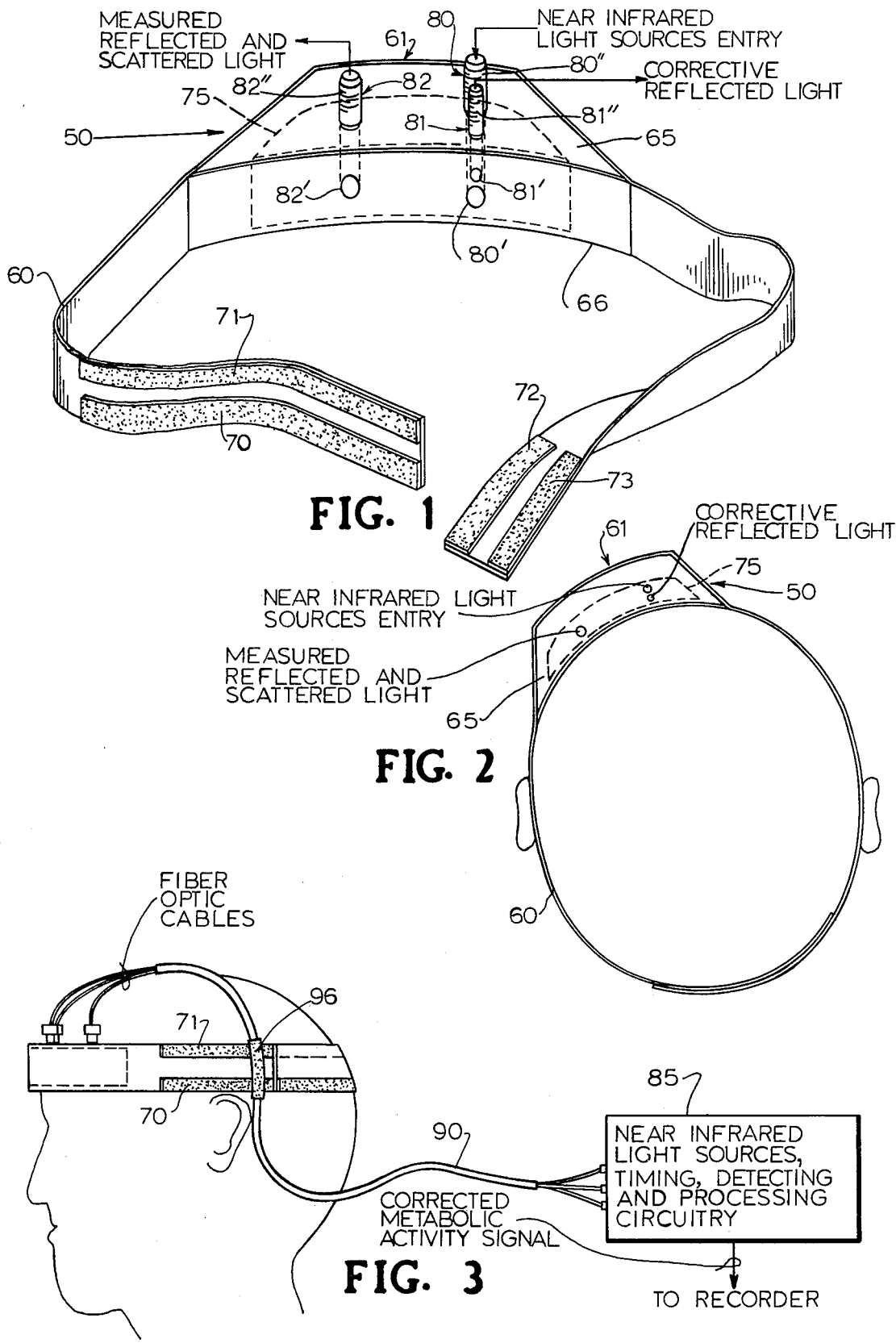

APPARATUS FOR MONITORING METABOLISM IN BODY ORGANS

The invention described herein was made in the course of work under a grant or award from the Department of Health, Education and Welfare.

DESCRIPTION

CROSS REFERENCE TO RELATED APPLICATIONS

This application relates to and constitutes a continuation-in-part of the subject matter of copending applications entitled "Method and Apparatus for Monitoring Metabolism in Body Organs", Ser. No. 810,777, filed June 28, 1977, now U.S. Pat. No. 4,281,645 and "Method and Apparatus for Monitoring Metabolism in Body Organs In Vivo", Ser. No. 017,727, filed Mar. 5, 1979, now U.S. Pat. No. 4,223,680, issued Sept. 23, 1980.

TECHNICAL FIELD

The invention relates to spectrophotometric apparatus for monitoring selected characteristics of the human body, in vivo.

BACKGROUND ART

In the prior copending applications there is described a spectrophotometric method and apparatus directed to non-invasive, continuous, atraumatic, in vivo, in situ monitoring of metabolism in a body organ. In the described applications, measuring and reference wavelengths within the near-infrared region, i.e., 700–1300 nm, are utilized for non-invasive, continuous, atraumatic, in situ, in vivo monitoring of oxidative metabolism by monitoring oxygen sufficiency in an internal organ, e.g., the brain or heart, of a human or animal body. Advantage is taken of the critical characteristic of cellular enzyme cytochrome a, $a_3$ (also known as cytochrome c oxidase and identified by EC 1.9.3.1) within the optical path and within the radiated portion of the selected organ for absorbing the selected measuring wavelength and for light of this measuring wavelength, as well as at least one reference wavelength within the same defined infrared region and at a low, non-hazardous level of intensity to be detectable at the end of a relatively long transillumination or reflectance path, e.g., of several centimeters length, which may include substantial content of bone as well as soft tissue and skin. Variations in metabolic and circulatory parameters during measuring are recognized and the selection of wavelengths, circuitry and method also provide techniques for compensating for changes in blood volume in the organ being monitored, for continuous monitoring of hemoglobin oxygenation and blood volume, for intermittent monitoring of blood flow rate, for skin blood flow effects and variations in the light source, i.e., laser diode, output.

In view of the fact that the prior art has been discussed extensively in the prior copending applications, such discussion will not be repeated here. The discussion to be found in the prior copending applications should thus be treated as incorporated herein by reference.

In the context of the mentioned prior copending applications and prior art, the present invention is primarily concerned with the light source and light detecting structure at the place of attachment to the body and with the means for mounting the light source-light detecting structure on the body. Thus, the present invention is intended to provide an improvement over the light source-light detecting structure shown, for example, in FIG. 3 of copending application Ser. No. 017,727 and FIG. 5 of copending application Ser. No. 810,777 as well as over all known prior art deemed relevant to the invention. A useful background of the prior art may be had by making reference to the light source and light detecting structures described in U.S. Pat. Nos. 3,527,932; 3,674,008; 3,638,640; 3,704,706; and 4,077,399.

Taking all of the foregoing into account, further development and experimentation with the spectrophotometric apparatus and method for measuring local metabolism described in the mentioned copending applications has revealed the need for an improved means for securing and shielding the light sources as well as the light detectors when attached to the body. Also, a need has arisen for simplifying the light source-light detecting structure which is attached to the body and to the associated mounting structure such that it can be made economically, in a disposable form and for a single end use application such as in a surgical operation, emergency accident situations and the like. Further, practical application of the spectrophotometric apparatus of the copending applications has indicated a need for being able to adjust the relative locations of the light sources and light detecting means on the body during monitoring. Additionally, needed improvements have been indicated in both the optical as well as the electronic structure associated with the monitoring apparatus at the place of attachment to the body. Finally, a need has been indicated for an improved means for being able to attach and detach the body-mounting structure containing the light source-light detecting means from the external light sources, control and processing circuitry.

The achievement of these various needed improvements thus becomes the general object of the invention and other objects will be revealed as the description proceeds.

DISCLOSURE OF INVENTION

The invention is directed to improvements in means for orienting in reference to the body, supporting on and attaching to the body, and shielding from ambient light at the point of attachment the light sources and the light detectors associated with remotely located spectrophotometric apparatus utilized for monitoring local metabolism in vivo, non-invasively and atraumatically according to the teachings of the related copending applications Ser. Nos. 017,727 and 810,777.

The invention apparatus is attached to the body, e.g., the head, a limb or to the torso, and operates with the apparatus and according to the techniques of the copending applications. Decisive information is provided on the parameter of oxygen sufficiency in the tissue or organ in question, in vivo. The invention apparatus when operating in conjunction with the apparatus and techniques of the copending applications also provides the capability of monitoring the oxygenation state of the blood being supplied, blood volume and blood flow rate in the portion of the body being monitored and in a manner which is non-invasive and atraumatic.

As distinct from the means for generating the near-infrared light sources, the timing, detecting and processing circuitry of the copending applications, the present invention is primarily concerned with improvements in the body-mounted light emitting and light detecting components and with improved means for detachably mounting, light shielding and orienting such light source-detecting components on the body and in a manner designed to avoid excessive localized pressure and erroneous signal conditions.

The body-mounted invention apparatus is utilized in association with the near-infrared sources, timing, detecting and processing circuitry as well as the measuring techniques described in the copending applications. Thus, by making reference to the subject matter of the copending applications, it will be understood that the present invention apparatus facilitates the carrying out of a continuous, non-invasive, in vivo, in situ monitoring of the redox state of cytochrome a, $a_3$ in the body portion of interest by using the deep, diffuse, multiple-scattered light, reflectance technique and near-infrared radiation within the range of about 700–1300 nm as referred to and fully described in the copending applications. When the invention apparatus is applied to the head, for example, the light source and light detector components are spaced apart on the same side of the head and the light reflected and scattered back to the light source location is detected and used in the associated processing circuitry of the copending applications as a correction for skin blood volume changes. The present invention apparatus is particularly advantageous in minimizing light loss and also minimizing the establishment of localized pressure conditions and thus avoiding erroneous signal conditions. The present invention apparatus also enhances the ability to discriminate between light scattered by the gray matter and light reflected from the white matter of the brain so as to provide a signal known to be indicative of the oxygen sufficiency in the gray matter of the brain.

With more specific reference to the actual structure employed in the improved light source-light detector body-mounted apparatus of the invention, there is provided a strap designed to be wrapped around a selected portion of the body, e.g., around the head, a limb or the torso, with the strap ends detachably secured for the purpose of supporting and orienting the light source, light detector, light shielding fiber optic and cable components of the invention. The mentioned strap mounts intermediate its length a block or section of resilient material adapted to conform to the shape of the body at the place of attachment and which also serves to embed terminal ends of the required light source and light detector elements. These terminal ends are adapted to be detachably connected by quick disconnect couplings to a cable assembly used to transfer light or light-related signals between the body-mounted apparatus of the invention and external apparatus providing the light sources, the timing, detecting and processing circuitry in which the desired spectrophotometric measurements are actually made according to the techniques of the copending applications.

All embodiments of the body-mounted invention apparatus provide means for detecting light reflected and scattered back from the location where the light first enters the body as well as separate means for detecting both scattered and reflected light at a point spaced from the light entry point. The invention apparatus also provides adequate light shielding to prevent entry of ambient light or other extraneous light signals and also in a manner designed to avoid the establishment of harmful localized pressure at those points where the light enters and is detected. Thus, correction for skin blood volume changes is provided in all embodiments by means of monitoring the light reflected back at the point of light entry in conjunction with using the light reflected and scattered back to the second point for processing according to the techniques of the copending applications.

In all embodiments, the incoming light is transferred to the body-mounted apparatus of the invention by means of an optical cable connected to the light source element of the body-mounted apparatus. In one embodiment, the corrective light reflected back from the body at the point where light from the light source enters the body as well as the measuring light reflected and scattered back to a point spaced from the light source are both detected and transmitted for processing by optical fiber means. In another embodiment, the corrective light as well as the measuring light are detected by photo-diodes and the corrective and measuring light is converted in the body-mounted apparatus to electrical signals having the corresponding light information and which are transmitted for processing by electrical cabling rather than optical cabling.

It is believed useful to recognize that reflectance may be categorized in at least three categories, i.e., (a) specular reflectance such as from a wet organ surface that glistens; (b) diffused, first surface reflectance productive of color and involving perhaps a few microns penetration; and (c) deep, diffuse reflectance which avoids specular and first surface reflectance and in which the photons penetrate at least one millimeter or more as in transillumination.

In the so-called "reflectance" mode described in copending application Ser. No. 17,727 of the original invention described in copending application Ser. No. 810,777, the trajectory of photons produces effects somewhat more closely resembling transillumination conditions than the more conventional first-surface reflectance conditions. In the former mode, a clear or relatively clear sample is transilluminated and spectrophotometric signals are assessed by measurements of light energy emerging from the side of the sample opposite to the surface of entry. Chemical analyses are typically performed in this mode. In conventional reflectance spectrophotometric measurements are made on light returning from the illuminated surface after extremely shallow penetration into the sample, say one thousandth of an inch or less. Such measurements are typically made to analyze the properties of pigmented paints. Generally, this produces a distortion of the absorption spectra of these pigments as extensively described in the technical literature (c.f. "Reflectance Spectroscopy" by W. W. Wendlandt & H. G. Hecht, Interscience Publishers, New York, 1966).

In the same-side illumination and detection mode of the copending application Ser. No. 17,727 both the "reference" or "corrective" signal and the "sample" or "measurement" signal are based on photons emerging on the same side of the body organ but having penetrated some considerable distance into tissue before being diffusely reflected and scattered back to the detectors. In the case of the reference signal, the majority of the photons has traversed some one to three millimeters through skin and bone whereas the sample light traverses several centimeters of tissue, such as skin, bone, gray matter and the skin and bone again before being collected by the detector device. With the foregoing discussion in mind and for lack of a better term, the reflectance techniques and reflectance mode described in the present and copending application Ser. No. 017,727 will therefore be referred to as "deep reflectance" recognizing that the results more closely resemble those obtained in the classical transillumination mode.

In one alternative embodiment, a detachable light shielding fabric is provided which can be formed as a light shielding cap, for example, when the invention apparatus is strapped to the head, or can be folded into other forms when other portions of the body, e.g., an injured limb, are being monitored. Another embodiment utilizes a photosensor and amplifying circuit in association with the light source such that electrical signals rather than optical signals are provided by the invention apparatus for processing in the circuitry described in the copending applications.

Another embodiment provides means by which the relative spacing between the light source and the light detector used for detecting light reflected and scattered from the organ or other body portion of interest can be varied for purposes of gaining the desired results in the most optimal manner. For example, variations in the size of human heads, limbs and torsos can be accommodated for by regulating the light source-measuring light detector spacing to suit the particular physical characteristics of each individual patient. Also, such adjustable spacing facilitates experimental research with the apparatus of the invention.

DESCRIPTION OF THE DRAWINGS

FIG. 1 is a pictorial view of the body mountable light source-light detector apparatus according to a first embodiment of the invention.

FIG. 2 is a plan view of the apparatus of FIG. 1 mounted on the head of a patient in a position typical for measuring oxygen sufficiency in the brain.

FIG. 3 is a side elevation view of the apparatus of FIGS. 1 and 2 and schematically illustrating how the body mounted apparatus of the invention is associated with the near-infrared light sources, timing, detecting and processing circuitry described in the copending applications.

BEST MODE FOR CARRYING OUT THE INVENTION

Figure 4:
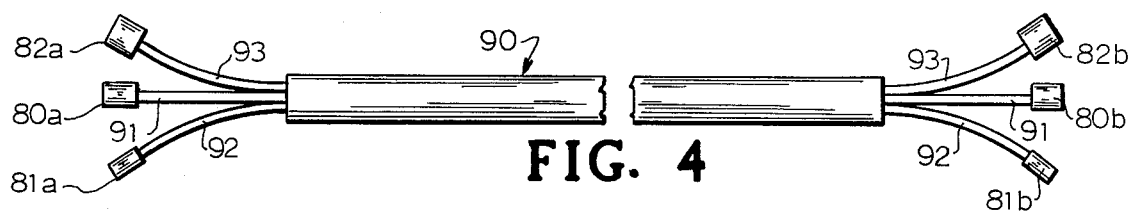
FIG. 4 is an enlarged, fragmentary, schematic view of the optical cable assembly used to connect the invention apparatus to the circuitry illustrated in FIG. 3.
Figure 5:
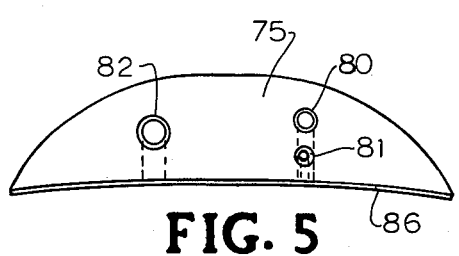
FIG. 5 is an enlarged plan view of an optical module employed in the apparatus of FIGS. 1 through 4.
Figure 6:
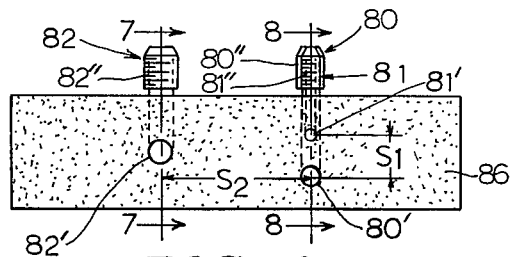
FIG. 6 is a front elevation view of the module of FIG. 5.
Figure 7:
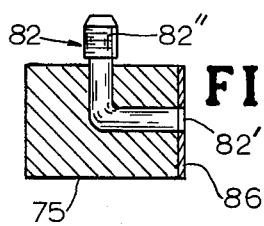
FIG. 7 is a section view taken along line 7—7 of FIG. 6.

As background for an understanding of the present invention, reference is again made to an observation set forth in the referred-to copending applications Ser. Nos. 810,777 and 017,727. Such observation is that light energy in the near-infrared region having wavelengths in the range of from about 700–1300 nm and at a relatively low, no-hazardous density can be made to penetrate both soft tissue and bone such as surrounds a living organ and in a relatively long optical path. Further, the reflected and scattered light at the end of the path can be detected and related to oxidative metabolism. This wavelength range has also proven critical since within the 700–1300 nm wavelength range oxygenated hemoglobin ($HbO_2$) has extremely low absorption characteristics, whereas disoxygenated hemoglobin (Hb) displays some weak absorption which slowly rises with decreasing wavelengths below 815 nm to a small peak in absorption around 760 nm. Because of these optical properties, the Hb-$HbO_2$ steady state (i.e., the venous-arterial average) can be monitored.

In addition and of significant importance, the prior copending applications also recognized that cytochrome a, $a_3$ in living body tissue also exhibits an oxygen dependent absorption band in the 700 to 1300 nm wavelength range of the spectrum. When this key enzyme in oxidative reactions is in the presence of sufficient oxygen, a weak absorption band exists with a maximum at a wavelength of about 820 to 840 nm. The absence of oxygen results in a complete reduction of the enzyme and a concomitant disappearance of the absorption band.

In carrying out a continuous, non-invasive, in vivo, in situ monitoring of the redox state of cytochrome a, $a_3$ according to the techniques described in the copending applications, near-infrared radiation of appropriate wavelengths and at a relatively low power level and corresponding relatively low density is presented at one site for transmission to the organ or other body portion under investigation, and the deeply reflected and scattered light emerging at another site is conducted to appropriate circuitry for detection and measurement as described in the copending applications. Also of importance is the observation that the deeply reflected light emitted at the point at which the near-infrared radiation first enters the body can also be detected and used as a means for compensating for skin blood volume changes at such point of light entry.

The techniques and apparatus described in the copending applications provide a capability using the deep reflectance technique for in vivo, in situ, non-invasive, atraumatic and continuous monitoring of four parameters of crucial significance related to metabolism of an organ or another body portion of interest. This capability is of special importance in situations where information on where information on the state of circulatory adequacy and oxygen sufficiency are needed. The four parameters which may be monitored separately or together include:

1. The adequacy of oxygen availability for normal function of cytochrome a, $a_3$, the cellular enzyme which mediates better than 90 percent of the oxygen consumed in living tissue.

2. The total blood volume in the tissue under investigation.

3. The steady-state status of the relative predominance of oxygenated hemoglobin ($HbO_2$), such as in arterial blood and disoxygenated hemoglobin (Hb) such as in venous blood in the tissue under investigation.

4. The blood flow rate in the tissue under investigation for relation to the foregoing parameters.

From the foregoing background description and by making reference to the more detailed description in the copending applications Ser. Nos. 810,777 and 017,727, it becomes evident that when the deep reflectance technique is followed, the means employed for introducing and implementing deep penetration of the near-infrared measuring and reference wavelengths at the point of light entry on the body, the means employed for collecting the directly and deeply reflected light at the point of light entry and the means for collecting the deeply penetrating light after being scattered and reflected from the organ, e.g., the brain, or other body portion of interest, are of crucial and significant importance to obtaining meaningful measurements of the parameters desired. It is desirable, for example, that the light source-light detector assembly which is attached to the body be in a form adaptable to various body shapes such as associated with the head, a limb, or torso of a human or animal subject under observation. It has also been found critically important that light shielding associated with the body-mounted light source-detector assembly be effective both as to extraneous near-infrared as well as extraneous ambient light such that the light entering the body as well as the light detected will be only those wavelengths and only from those light sources intended to be associated with the measurements. Extraneous photon energy at the measuring location which might otherwise enter the body and affect the measurements is therefore desirably absorbed by means associated with the light source-detector assembly of the invention.

It has also become evident that the light source-detector assembly which attaches to the body must be in a form which avoids restricting local blood flow or any other tissue function in the area of observation so as to avoid erroneous signals. Additionally, it has been found desirable that the light source-detector elements have a body mounting arrangement that not only lends itself to shielding of extraneous light but also protects the elements as the mounting assembly changes to conform to the body shape at the area of observation. Another critical feature in the light source-detector element mounting structure is that the relative space between the light source and detector elements remain fixed during the measuring period and not be subject to alterations by physical changes in body geometry brought about by breathing, flexing of the body, trauma, and the like. Another major consideration is that the light source-detector assembly which is mounted on the body be in a form adapted to be quickly coupled and uncoupled to the timing, light source, detecting and processing circuitry typically located at least several feet away from the patient.

As another important consideration, it has been found highly desirable that the light source-detector assembly which attaches to the body be in a form lending itself to economical manufacture so as to be adapted to a single end use and useful as a disposable component. Considering the difficulty and cost of washing and sterilization, the possibility of transmitting diseases and the likelihood of contamination in surgical and accident cases in particular, the advantage of having a prepackaged, sterilized, single end use, disposable light source-detector assembly will be readily appreciated.

With the foregoing background information and desired characteristics and objectives in mind, the description next makes reference to the drawings to illustrate how the same are achieved in the body-mounted light source-light detector assembly of the invention.

Referring initially and principally to FIGS. 1–10, the light source-detector assembly 50 of the invention comprises a base support strap 60 preferably formed of a tightly woven, elastic fabric such as found, for example, in elastic straps, stretchable belts, elastic fabric, and the like. Strap 60 should preferably have an ability to stretch while providing sufficient flexibility to conform to the shape of the head, limb or torso of a human or animal subject under investigation while keeping the distance between modules 80 and 82 relatively fixed. The chief means of attachment of the body part, i.e., strap 60, includes an intermediate portion 61 surrounding and adhered to the outer side surfaces of what will be referred to as the module container 65. A flexible but inextensible inner strap 66 is adhered at its ends to strap 60 as best illustrated in FIGS. 1 and 2. The inner surface of strap 66 is also adhered to the inner side surface of module container 65 whose thickness is preferably substantially equal to the width of straps 60, 61 as shown. Straps 60 and 61 thus act as a support for module container 65 enabling it to be supported on selected portions of the body as illustrated, for example, in FIGS. 2, 3, 16 and 17 in an outwardly protruding position. Strap 60 being constructed of a tightly woven extensible and elastic material provides pressure for closely applying module 75 held by container 65.

All surfaces of straps 60 and 66 are preferably black in color to assist in absorbing extraneous photon energy proximate to the observation area. The body strapping and unstrapping operation utilizing strap 60 is facilitated by employment of mating "Velcro" type strips 70–73 on the corresponding mating surfaces of strap 60 such that strap 60 can easily conform to the size and shape of body contour where the light source-detector assembly 50 is attached for monitoring purposes as illustrated in FIGS. 2–3, 14–15 and 16–17.

Module container 65 is preferably molded of a relatively soft, deformable material such as soft silicone rubber and surrounds and embeds a separately constructed component referred to as the optical module 75. Module 75 is also preferably formed of a relatively soft, deformable material such as soft silicone rubber and is assembled with the three illustrated light guides, namely, light source terminal 80, corrective light detector terminal 81 and measuring light detector terminal 82 before being embedded in the module container block 65.

Light source terminal 80 comprises a preformed L-shaped fiber optics guide and provides a path of light entry for the near-infrared measuring and reference wavelengths supplied by the circuitry 85 constructed as described in the previously-referred to copending applications. The optical face 80' of optical terminal 80 is positioned so as to provide through a layer of light shielding material 86 (FIGS. 5–8) adhered to module 75 and is also exposed through a suitable opening provided in inner strap 66 as illustrated in FIG. 1.

Utilizing a similar construction, light detector terminal 81 comprises a pre-formed L-shaped fiber optics bundle-guide and provides a path of light exit proximate the point of light entry for receiving light which is reflected back directly towards optical face 81' and which is processed by circuitry 85 for skin blood volume change compensation as previously mentioned. As with light source terminal 80, light detector terminal 81 has its optical face 81' positioned so as to protrude through a layer of light shielding material 86 (FIGS. 5–8) adhered to module 75 and is also exposed through a suitable opening provided in inner strap 66 as further illustrated in FIG. 1.

In a similar construction, optical terminal 82 comprises another preformed L-shaped fiber optics bundle-guide The optical face 82' of optical terminal 82 is spaced apart from the point of light entry associated with optical face 80' of light source terminal 80 and serves as a means for collecting the reflected and scattered light from the body organ, e.g., the brain, or other body portion being observed. Such measured scattered and reflected light is thus transmitted through optical terminal 82 to the circuitry 85. As with the light source terminal 80 and light detector terminal 81, the optical face 82' of optical terminal 82 is positioned so as to protrude through a layer of light shielding material 86 (FIGS. 5–8) adhered to module 75 and is also exposed through a suitable opening provided in inner strap 66 as best seen in FIG. 1.

Figure 10:
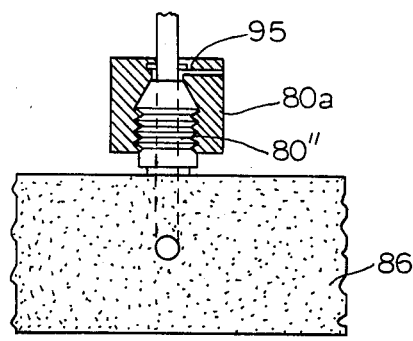
FIG. 10 is an enlarged fragmentary section view illustrating a connector arrangement employed in making optical connections with the optical cable assembly of FIG. 4.

Light source terminal 80, corrective light detector terminal 81 and measuring light detector terminal 82 are purposely provided with different size appropriately-threaded coupling ends 80", 81" and 82" to prevent improper connections to appropriate points associated with the circuitry 85. To further facilitate the interconnection between circuitry 85 and the light source-detector assembly 50 of the invention, an optical cable assembly 90 is provided with optical cables 91, 92 and 93. One end of the respective optical cables 91–93 is provided with threaded coupling caps 80a, 81a, and 82a for securing to the respective terminal coupling ends 80", 81" and 82". The opposite end of optical cable assembly 90 is provided with appropriately threaded coupling caps 80b, 81b, and 82b for making a quick connect-disconnect coupling to the circuitry 85 as illustrated, for example, in FIG. 3. The respective couplings as illustrated in FIG. 10 are preferably made using conventional optical fiber coupling techniques with a conventional optical gel and with each coupling cap, such as cap 80a illustrated in FIG. 10, having a gel exit passage 95 through which excess gel may pass when the coupling is completed. When in use as illustrated in FIG. 3, the cable assembly 90 is fitted with an adjustably positioned tubular "Velcro" surfaced pad 96 adapted for releasable attachment to the mating "Velcro" surfaced strips 70, 71.

Figure 11:
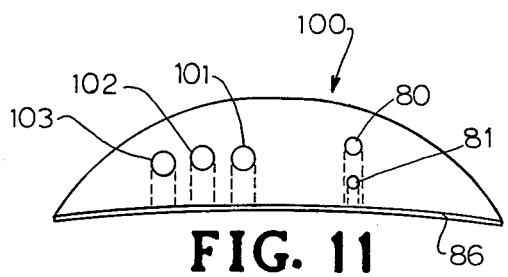
FIG. 11 is a plan view of a second embodiment of the optical module of FIG. 5 and formed such that the distance between light entry and exit locations can be changed.

The spacing, S-1 between the optical faces 80' and 81' has been found to affect the quality of measurements obtained with the invention. Therefore, it is desirable that the spacing S-1 not exceed one centimeter. Another spacing critical to the invention operation is the relative spacing S-2 between the point of light entry, optical face 80' of light source terminal 80 and the point of collecting the measured reflected and scattered light, i.e., optical face 82' of measuring light detector terminal 82. The criticality of the S-1 and S-2 spacing will be better understood in reference to FIG. 9 as later explained. In order for the invention apparatus to accommodate to a relatively wide range of body contours and also for research and experimental purposes, it has been found desirable to provide an optical module adapted such that the spacing S-2 between the points of light entry and exit can be changed. In this regard, a modified (FIG. 11) optical module 100 is formed with the light source terminal 80 and the corrective light detector terminal 81 preformed and positioned in optical module 100 in the same manner as previously described with reference to FIGS. 1–3 and 5–8. However, optical module 100 allows the position of the measuring light detector terminal to be changed according to need and thus allows the spacing S-2 to have some degree of adjustment. As best illustrated in FIG. 11, optical module 100 provides three pre-molded cavities 101, 102 and 103 designed to resiliently receive, grip and position the measuring light detector terminal 82 in any of the three corresponding positions, the significance of which will become more apparent in connection with later explanation of FIG. 9.

Figure 13:
FIG. 13 represents a cross section taken on line 13—13 of FIG. 12 through a combined light source and reference detector bundle.
Figure 12:
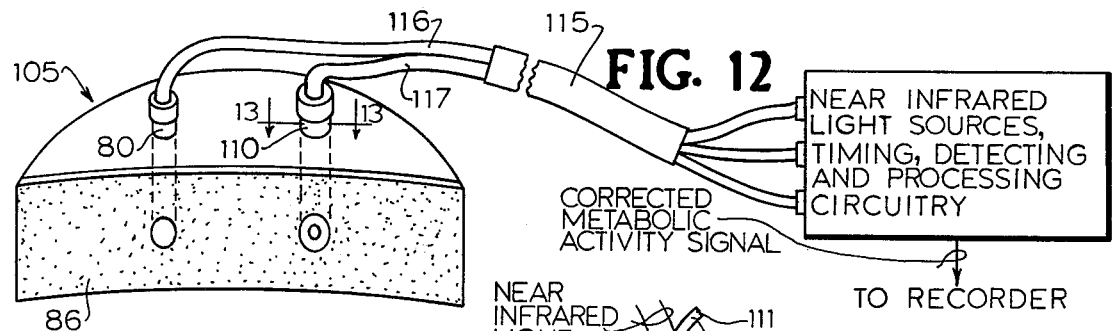
FIG. 12 is a pictorial view illustrating in a third embodiment, a modified optical module and cable assembly based on using a combined light source and reference detector bundle.

In another variation of the invention, a modified optical module 105 is provided in which the light source terminal and corrective detector terminal are combined into a single preformed, optical fiber terminal structure 110 as shown in FIGS. 12–13. Terminal structure 110 comprises an inner fiber bundle 111 which is employed for collecting the light reflected back directly from the point of light entry, corresponding to the purpose of corrective light detector 81, and an outer fiber bundle 112 which is employed for presenting the near-infrared light sources to the body, corresponding in function to light source terminal 80. Thus, in operation, the directly reflected corrective light and the measured reflected and scattered light follow the paths schematically illustrated in FIG. 12A using brain monitoring by way of example. When using the combined light source-like detector terminal arrangement illustrated in FIGS. 12-13, a modified wiring assembly 115 is employed having a pair of corresponding optical cables 116, 117 connected to the circuitry 85 as further illustrated in FIG. 12.

In another variation, not illustrated, the light collecting fibers for corrective detection are randomly interspersed among the fibers bringing the near-infrared energy to the body organ, separation of the two sets of intermixed fibers occurring only at the circuitry 85 as illustrated in FIG. 12.

Figure 14:
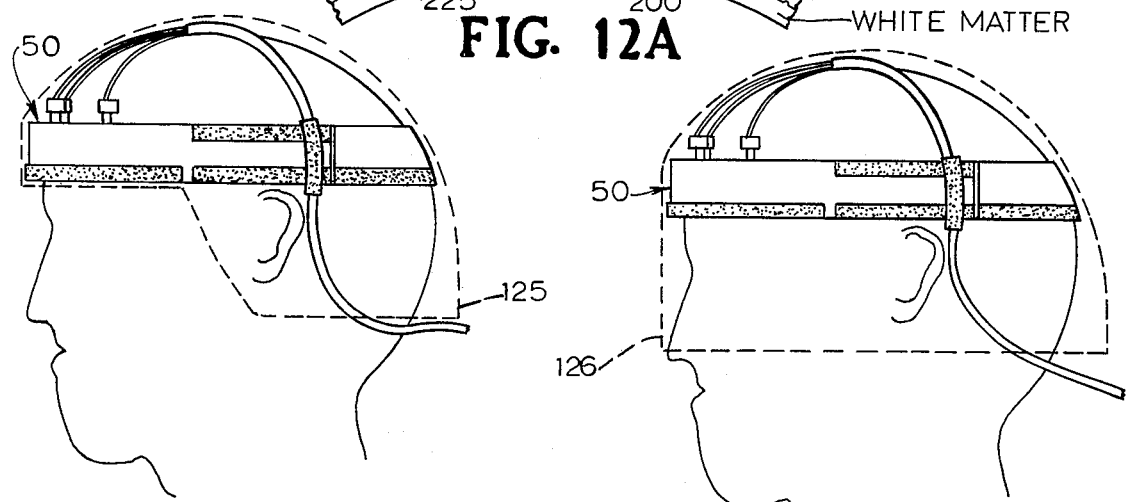
FIG. 14 is a side elevation view similar to that of FIG. 3 illustrating in a fourth embodiment and in dashed lines a head covering light shielding drape detachably secured to the invention apparatus.
Figure 15:
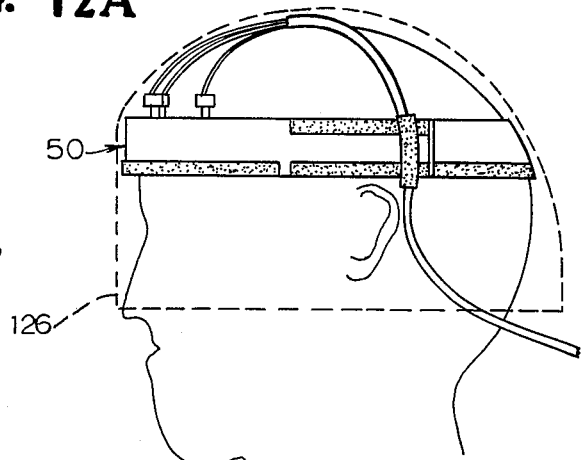
FIG. 15 is a side elevation view similar to that of FIG. 3 illustrating in a fifth embodiment another form of light shielding drape adapted to cover both the head and the upper portion of the face of the patient.
Figure 16:
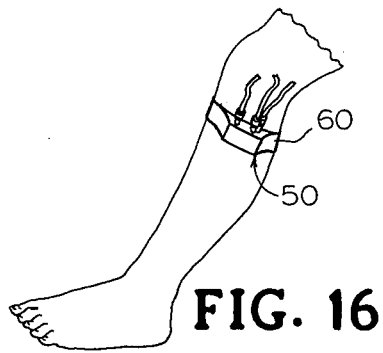
FIG. 16 is a pictorial view of the apparatus of FIG. 1 mounted on the leg of a patient for monitoring purposes.
Figure 17:
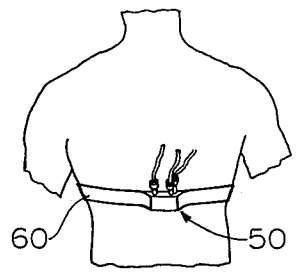
FIG. 17 is a pictorial view of the apparatus of FIG. 1 mounted on the abdomen of the patient for monitoring.
Figure 18:
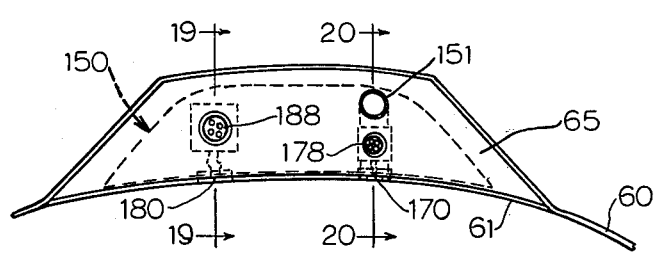
FIG. 18 is a fragmentary plan view of the invention apparatus illustrating in a sixth embodiment an optical module having photo diode light detecting apparatus incorporated as part of the module construction.
Figure 19:
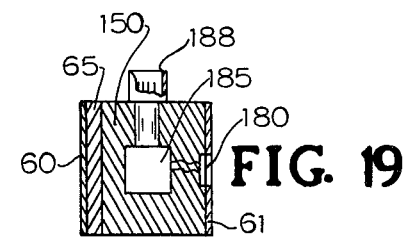
FIG. 19 is a section view taken along line 19—19 of FIG. 18.
Figure 20:
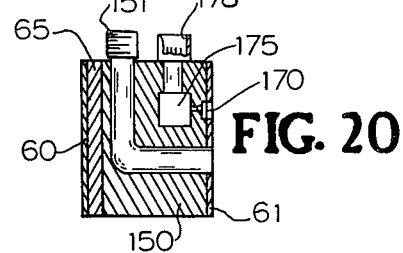
FIG. 20 is a section view taken along line 20—20 of FIG. 18.
Figure 21:
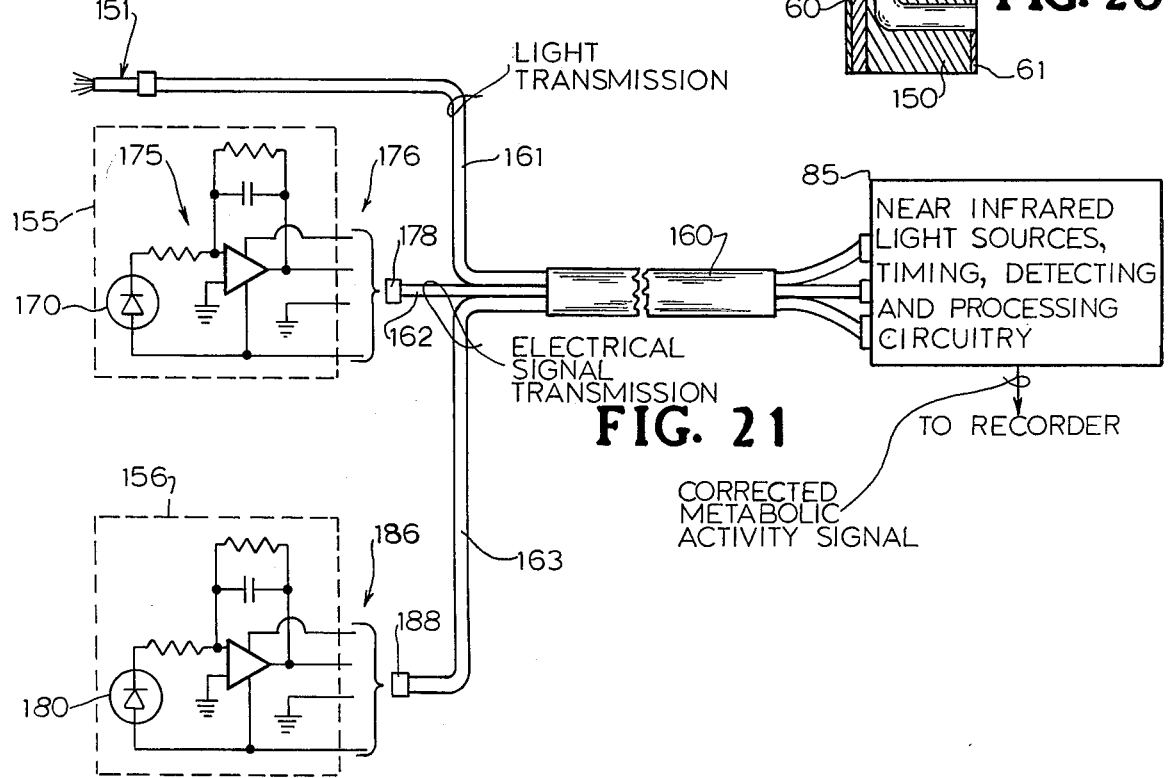
FIG. 21 is a schematic diagram of the optical module components of FIG. 18 connected to the circuitry employed for processing the optical and electrical signals during monitoring.

Shielding of ambient light is deemed important especially when metabolic trends are being monitored and discrete changes are significant though small in value. Thus, shielding of extraneous signals becomes important. For this purpose, as illustrated in FIGS. 14-15, a flexible light shielding fabric such as a tightly woven black cloth fabric, black coated Mylar film, or the like, is provided with internal "Velcro" surfaced strips, not shown, enabling either the head type cape 125 or the head and face type cape 126, both being indicated in dashed lines, to be installed as illustrated dependent on the source and direction of ambient light. With such shielding, extraneous light and therefore extraneous signals can essentially be eliminated.

Figure 8:
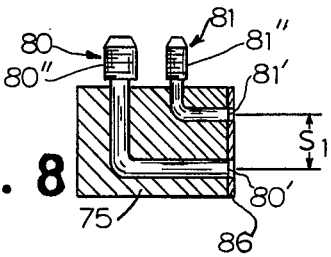
FIG. 8 is a second view taken along line 8—8 of FIG. 6.
Figure 8A:
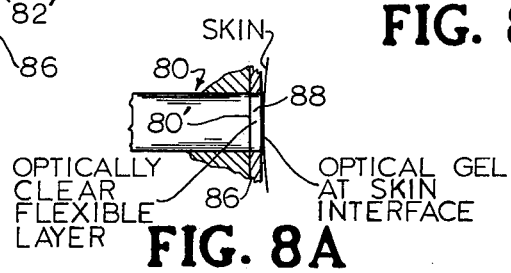
FIG. 8A is an enlarged partial section view of a typical optical face having a resilient optically clear cap to accommodate to body contour.

Close coupling of the skin with the light source and light detecting means at those points where light enters and exits is also of critical importance. In this regard and as best illustrated in FIG. 8A, the light guide surfaces 80', 81', 82' of the fiber optics terminals 80, 81 and 82 as well as the later-described light receiving surfaces of photo diodes 170, 180 of the signal detection modules 155, 156 are covered by a cap 88 made of a soft, optically clear, deformable material adapted to promote good contact between each respective optical face and the skin by appropriate deformation under the pressure provided by strap 60. A suitable material for cap 88 has been found to be a silicon compound sold under the Dow Chemical trademark "Sylgard". Such arrangment has been found to produce improved optical coupling with the skin and consequently increased signal levels. Application of an optical coupling gel between each cap 88 and the skin at the point of contact further enhances the signal coherence as indicated in FIG. 8A.

In each of the invention embodiments thus far described, the light detection is accomplished by means of optical fiber terminals, i.e., corrective light detector terminal 81 and measuring light detector terminal 82. Thus, with the previously described embodiments, light, in the near-infrared range of wavelengths, is transmitted to the light source-detector assembly 50 of the invention and light signals are transmitted from the assembly 50 to the circuitry 85 for processing. In an alternative embodiment illustrated in FIGS. 18-21, the light detection in the body-mounted assembly 50 of the invention is effected making use of photo diodes and photo diode circuitry embedded in the assembly 50 such that both the corrective detected light as well as the measured detected light is transmitted as electrical signals rather than optical signals for processing in the circuitry 85.

Making more specific reference to FIGS. 18-21, the alternative optical module 150 is embedded in the module container 65 as previously explained. A light source terminal 151, comparable to light source terminal 80, shown in FIGS. 1-8, is employed and is basically arranged and functions in the same manner as previously explained. However, in place of the corrective light detector 81, i.e., a fiber optic bundle as employed in the optical module 75 of FIGS. 1-8, there is employed an electrical assembly having a photo diode detector circuit 155 providing electrical signals related to light reflected back at the point of light entry and used for skin blood volume compensation. Also, in place of the measuring light detector 82 illustrated in FIGS. 1-8, there is employed another electrical assembly having a photo diode circuit 156 which provides electrical signals related to the scattered and reflected light to be measured by the circuitry 85. In this photo diode based embodiment of the invention, the modified connecting cable assembly 160 thus combines an optical fiber cable 161 and a pair of electrical signal carrying cables 162, 163.

The photo diode circuitry 155 includes a photo diode 170 and a suitably housed conventional filter-amplifying circuit 175 which through connecting wires 176 provide electrical signals related to the light reflected back at the point of light entry and which through a suitable connector 178 are transmitted to the circuitry 85 by means of electric cable 162 for utilization in compensating for skin blood volume changes at the measuring location as previously referred to.

Photo diode circuit 156 includes a similar photo diode 180 and a suitably housed conventional filter-amplifying circuit 185 which through connecting wires 186 provide electrical signals related to the collected reflected and scattered light from the organ or other body portion being observed and which is measured by the circuitry 85. Utilizing a suitable electrical connector 188, such signals are transmitted to circuitry 85 by means of electric cable 163 as representing such collected reflected and scattered light.

In comparing the completely optical type module as illustrated in FIGS. 1-8 and 10-12 with the photo diode light detecting type module as illustrated in FIGS. 18-21, it will, of course, be appreciated that the circuitry 85 will necessarily be adapted in the case of optical signals for processing optical signals and converting the same to electrical signals and in the case of receiving electrical signals will be adapted to process the signals in such form. That is, the circuitry 85 such as illustrated in FIG. 3 and FIG. 12 will necessarily include optical to electrical conversion circuitry which is not required in the case of handling the electrical signal information produced by the respective photo diode circuits 155, 156 in FIG. 21.

Figure 12A:
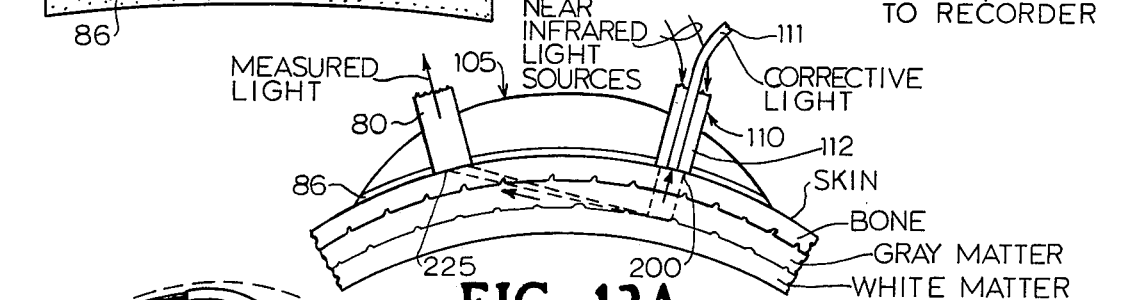
FIG. 12A diagramatically illustrates use of the optical module arrangement of FIG. 12 as applied using the reflectance technique to the head of a human or animal, in vivo.

From what has thus far been described, it will be seen that the invention body-mounted light source-light detector apparatus provides improved means for admitting, shielding and detecting the deeply reflected and scattered near-infrared measuring and reference wavelengths associated with practicing the deep reflectance technique according to the teachings of the previously referred to copending applications Ser. No. 810,777 and Ser. No. 017,727. Using brain monitoring as an example and the type of optical module illustrated in FIGS. 12-13 as being employed in the invention light source-detector assembly 50 and with reference to the schematic diagram of FIG. 12A, the invention is employed by first choosing two spaced apart locations, one of which may be designated as a point of light entry 200 and the other of which may be designated as a point of light exit 225 as indicated in FIG. 12A. Advantageously, any bare or bald skin area of sufficient size (one centimeter square approximately) can be used as an entry or exit site without preparation. As later explained in reference to FIG. 9, the spacing between the light entry point 200 and light exit point 225 is critical for purposes of the invention and particularly so in reference to utilizing the invention in the manner described for measuring local metabolism in the brain of a living human.

With continued reference to the optical module construction illustrated in FIGS. 12-13 and the schematic representation in FIG. 12A, light from the light sources associated with circuitry 85 is transmitted to the light entry location 200 through the fiber optics bundle assembly 110 having the outer annular fiber bundle assembly 112 surrounding the inner central smaller bundle assembly 111 or having the entry and corrective fibers randomly interspersed as previously mentioned. Utilizing the strap and optical module mounting arrangement of the invention, the proximal end, i.e., deformable cap 88, of the assembly 110 is located in a tightly pressed and light shielded position against the light entry location 200 so as to minimize leakage and loss of light at the point of entry.

The general concentric arrangement of the outer annular fiber optics bundle 112 and central fiber optics bundle 111 are shown in the cross section drawing illustrated in FIG. 13. The outer bundle 112 will be noted as providing a means for transmitting near-infrared light within the designated spectral range to the point of light entry 200 so as to provide photons capable of deep penetration including the skin and bone layer as well as the gray matter and white matter schematically illustrated in FIG. 12A. Those deep penetrating photons which are directly reflected upwardly from tissues below the light entry assembly 200 or within a few millimeters of that point of entry are transmitted through the inner optic bundle 11 to an appropriate reference detector forming part of circuitry 85. Other photons are transmitted, reflected and scattered through and by the skin and bone structure, through and by the gray matter to and from the white matter and in association with relatively deep penetration to provide a continuous number of such photons reaching the point of light exit 225 where they are picked up by the other single fiber optics bundle 80 and transmitted to a measuring detector forming part of circuitry 85, with the output of such reference and measuring detectors being directed to suitable processing circuitry within circuitry 85 for conversion to a signal indicative of oxygen sufficiency in the gray matter utilizing the techniques previously described in the referred to copending applications.

Figure 9:
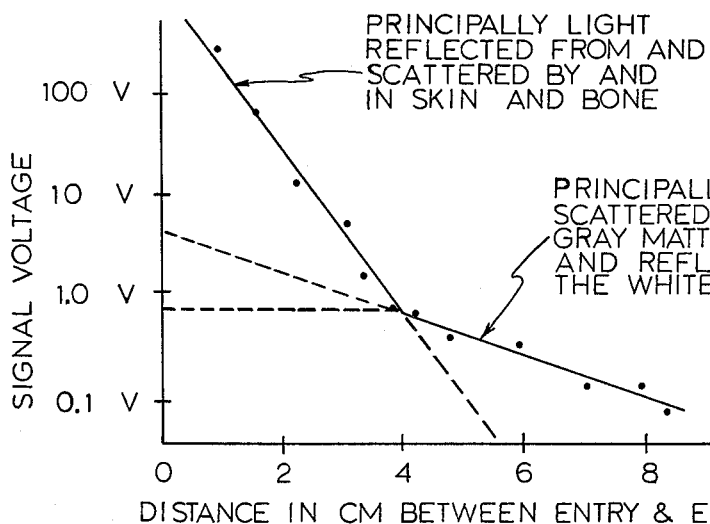
FIG. 9 is a plot of the relation of the distance between light entry and exit locations to the signal voltage and the source of the measured light when using the reflectance technique as in FIG. 2.

With special reference to FIG. 9, it will be noted that the spacing between the points of light entry and exit 200, 225 has a significant relation to the source of photons which are picked up through the fiber optics bundle 80 and transferred to the mentioned measuring detector. For example, it will be seen that when the distance S-1 between the points of light entry and exit 200, 225 is less than approximately 4.25 centimeters that the photons reaching the exit point 225 will consist of light principally made up of photons scattered by and in the skin and bone. In contrast, it will be noted in reference to FIG. 9 that when the spacing S-1 between the points of light entry and exit 200, 225 is greater than approximately 4.25 centimeters that the photons reaching the fiber optics bundle assembly 80 will consist principally of light scattered by and in the gray matter of the brain. Thus, by using the inner fiber optical bundle 111 to receive light directly reflected and scattered upwards, photons reflected from the skin and bone will predominate as further indicated by FIG. 9 and using this as a reference to the measuring detector in the circuitry 85, a signal can be obtained which is sufficiently accurate to represent oxygen sufficiency in the gray matter. Further, the photons representing those which have been scattered and reflected by the skin and bone and detected by the reference detector may be used for signal stabilization against variations in light output of the light sources in circuitry 85 and, importantly, for correction for skin blood volume changes to achieve the desired corrected metabolic activity signal.

We claim:

1. A spectrophotometric reflectance apparatus for measuring in situ, in vivo, non-invasively, atraumatically, harmlessly, rapidly and continuously a local metabolic oxygen dependent activity of a selected portion of the body such as the brain of a body where such activity bears a measureable relation to an oxygen dependent absorption characteristic of the selected portion for a particular wavelength of light transmitted therethrough, comprising:

(a) circuitry means including:
   (i) a plurality of near-infrared light sources located external of the body and having light emissions of different wavelengths in the 700 to 1300 nanometer spectral range and of an intensity below the level damaging to the body and said selected portion but sufficient to be detectable by a light sensor after transmission through any skin, bone and tissue included in an optical transmission-reflectance path including said selected portion thereof and extending for several centimeters between points of light entry and exit laterally spaced several centimeters apart and located on contiguous skin surface areas of the body and after scattering in and deep reflectance from said selected portion along said path, said emissions including at least one measuring wavelength and at least one reference wavelength within said spectral range, each said measuring wavelength being selected such that said selected portion exhibits a selected absorption therefore, the extent of which is dependent upon a specific state of a local metabolic, oxygen dependent activity of said selected portion; and
   (ii) means operatively associated with said light sources to produce emissions representing at least one said measuring wavelength and at least one said reference wavelength within said spectral range for transmission along said path to said selected portion and at levels of intensity below that which would be damaging to the body and said selected portion;

(b) first optical cable coupling means for receiving transmitting and directing the output light emissions of said light sources at said measuring and reference wavelengths to a light entry point proximate said body;

(c) a detachable, body mountable apparatus associated with said circuitry means including:
   (i) a flexible, elongated support member adapted to be releasably secured to the body proximate a said selected portion of the body having a selected set of said light entry and exit points, said support member being adapted to provide ambient light shielding over said light entry and exit points and to conform to the curvature and shape of the body at the location thereof;

(ii) a mounting structure secured to said support member and adapted to deform in shape in correspondence with the curvature assumed by said support member when secured to the body;

(iii) a first preformed light guide means mounted in said mounting structure and optically coupled to said first optical cable means and having an optical face for light exit adapted to be mated in a substantially pressed fit relation with said selected point of light entry for entry of light in said wavelengths to be transmitted, deeply reflected and scattered along said path and to said selected portion;

(iv) a first preformed light detector assembly mounted in said mounting structure proximate said first light guide means and having first light collector means adapted to be mated in a substantially pressed fit relation with said selected point of light entry for receiving deeply penetrating light emissions reflected directly back from any skin, bone and tissue at or within a few millimeters of said selected point of light entry; and (v) a second preformed light detector assembly mounted in said mounting structure and having second light collecting means spaced several centimeters away from said first collector means and adapted to be mated in a substantially pressed fit relation with said selected point of light exit for receiving deeply penetrating light emissions reflected and scattered to said selected point of light exit from said selected portion of said body;

(d) second coupling means operatively coupling the output of said first light detector assembly to said circuitry means;

(e) third coupling means operatively coupling the output of said second light detector assembly to said circuitry means; and (f) processing means operatively associated with said circuitry means adapted to produce from the outputs of said first and second light detector assemblies an electrical output signal corrected for changes in blood volume of said skin, bone and tissue during the measuring cycle and representing the difference in absorption of said measuring and reference wavelengths by said selected body portion as a function of the state of said local metabolic oxygen dependent activity and further adapted to convert said electrical output signal to a signal providing a substantially continuous and rapid measure of said activity.

2. An apparatus as claimed in claim 1 wherein said support member is formed as an elastic strap with adjustable securing means thereon, said mounting structure is secured to said strap in a manner enabling said strap when mounted on said body to exert pressure on said mounting structure and thereby orient said first light guide means optical face and said first and second light detector assemblies' first and second light collector means in said press fit relation with respect to said selected light entry and exit points.

3. An apparatus as claimed in claim 1 wherein said first and second light collector means comprise second and third preformed light guide means with light collecting optical faces thereon and being mounted in said mounting structure, and said second and third coupling means comprise second and third optical cable means connected to said second and third light guide means.

4. An apparatus as claimed in claim 3 wherein said first preformed light guide means and said second preformed light guide means are formed as an integral coaxial optical cable terminal.

5. An apparatus as claimed in claim 1 wherein said first and second light collector means comprise photo diode means and said first and second light detector assemblies include associated circuitry for converting light emissions received by said photo diodes to electrical signals representative thereof and said second and thid coupling means comprise a pair of electrical cabling means operatively connected to the respective said assemblies for conducting said photo diode developed signals to said circuitry means.

6. An apparatus as claimed in claim 1 including auxiliary ambient light-shielding means in the nature of a flexible cap adapted to cover said selected portion of the body and to be detachably secured to said support member.

7. An apparatus as claimed in claim 1 wherein said mounting structure is formed in a manner enabling the spacing between said first light guide means and said second light detector assembly to be adjusted.

8. An apparatus as claimed in claim 1 wherein said first light guide means and said first light detector assembly comprise a single integral preformed optical cable terminal with selected optical fibers and the faces thereof being allocated and adapted to be utilized for transmitting and entry of light in said wavelengths to said point of entry with the remainder of the optical fibers and the faces thereof being allocated and adapted to be utilized for receiving said light emissions reflected directly back from any skin, bone and tissue at or within a few millimeters of said selected point of light entry and wherein said first and second coupling means comprise optical cable means coupled at one end to said single cable terminal and at the opposite end being branched with separate couplings to said circuitry means with those fibers allocated to transmitting said wavelengths to said point of light entry having one coupling to said circuitry means and with the said remainder of said optical fibers having another coupling for transmitting said light emissions to said circuitry means.

9. An apparatus as claimed in claim 1 wherein said first light guide means and said first and second light detector assemblies are provided with operatively associated detachable coupling means enabling said body mountable apparatus to be installed on and removed from the body as a unitary replaceable structure.

10. An apparatus as claimed in claim 1 including resilient capping means effective under the pressure of said support member to establish resilient body conforming light guides adjacent the skin adjacent each said point of light entry and exit.

11. In a spectrophotometic reflectance apparatus for measuring in situ, in vivo, non-invasively, atraumatically, harmlessly, rapidly and continuously a local metabolic oxygen dependent activity of a selected portion of the body where such activity bears a measurable relation to an oxygen dependent absorption characteristic of the selected portion for a particular wavelength of light transmitted therethrough having:

(a) circuitry means including:

(i) a plurality of near-infrared light sources located external of the body and having light emissions of different wavelengths in the 700–1300 nanometer spectral range and of an intensity below the level damaging to the body and said selected portion but sufficient to be detectable by a light sensor after transmission through any skin, bone and tissue included in an optical transmission-reflectance path including said selected portion thereof and extending for several centimeters between selected points of light entry and exit laterally spaced several centimeters apart and located on contiguous skin surface areas of the body and after scattering in and deep reflectance from said selected portion along said path, said emissions including at least one measuring wavelength and at least one reference wavelength within said spectral range, each said measuring wavelength being selected such that said selected portion exhibits a selected absorption therefore, the extent of which is dependent upon a specific state of a local metabolic, oxygen dependent activity of said selected portion; and (ii) means operatively associated with said light sources to produce emissions representing at least one said measuring wavelength and at least one said reference wavelength within said spectral range for transmission along said path to said selected portion and at levels of intensity below that which would be damaging to the body and said selected portion;

(b) first optical cable means providing a bundle of optical fibers with selected fibers connected for receiving, transmitting and directing the output light emissions of said light sources at said measuring and reference wavelengths to a selected light entry point proximate said body and other selected fibers connected for receiving deeply penetrating light emissions reflected directly back from any skin, bone and tissue at or within a few millimeters of said selected point of light entry and coupling such emissions to a processing means;

(c) second optical cable means providing a bundle of optical fibers adapted for receiving deeply penetrating light emissions reflected and scattered to said selected point of light exit from said selected portion of said body and coupling such exit light emissions to a processing means; and (d) processing means operatively associated with said circuitry means adapted to produce from the outputs of said first and second optical cable means an electrical output signal corrected for changes in blood volume of said skin, bone and tissue during the measuring cycle and representing the difference in absorption of said measuring and reference wavelengths by said selected body portion as a function of the state of said local metabolic oxygen dependent activity and further adapted to convert said electrical output signal to a signal providing a substantially continuous and rapid measure of said activity;

(e) an improved detachable, body mountable apparatus associated with said circuitry, coupling and processing means comprising:

(i) a flexible, elongated support member adapted to be releasably secured to the body proximate a said selected portion of the body having a selected set of said light entry and exit points, said support member being adapted to provide ambient light shielding over said light entry and exit points and to conform to the curvature and shape of the body at the location thereof;

(ii) a mounting structure secured to said support member and adapted to deform in shape in correspondence with the curvature assumed by said support member when secured to the body;

(iii) a first preformed right angled light guide means supported in said structure and formed by a bundle of optical fibers optically coupled to said first optical cable means and having an optical face adapted to be mated in a substantially pressed fit relation with said selected point of light entry utilizing selected fibers of said bundle for entry of light in said wavelengths to be transmitted, deeply reflected and scattered along said path and to said selected portion and other selected fibers for receiving deeply penetrating light emissions reflected directly back from any skin, bone and tissue at or within a few millimeters of said selected point of light entry; and (iv) a second right angled light guide means formed by a bundle of optical fibers optically coupled to said second optical cable means and having a second optical face spaced several centimeters away from said first optical face and adapted to be mated in a substantially pressed fit relation with said selected point of light exit for receiving deeply penetrating light emissions reflected and scattered to said selected point of light exit from said selected portion of said body.

* * * * *